United States Patent
Capello et al.

(10) Patent No.: US 8,477,192 B2
(45) Date of Patent: Jul. 2, 2013

(54) OPTICAL DETECTION SYSTEM FOR MOTOR-VEHICLES HAVING MULTIPLE FUNCTIONS, INCLUDING DETECTION OF THE CONDITION OF THE ROAD SURFACE

(75) Inventors: Davide Capello, Orbassano (IT); Nereo Pallaro, Orbassano (IT); Luca Liotti, Orbassano (IT); Cosimo Carvignese, Orbassano (IT)

(73) Assignee: C.R.F. Societa Consortile per Azioni, Orbassano (Torino) (IT)

( * ) Notice: Subject to any disclaimer, the term of this patent is extended or adjusted under 35 U.S.C. 154(b) by 455 days.

(21) Appl. No.: 12/891,083

(22) Filed: Sep. 27, 2010

(65) Prior Publication Data

US 2011/0149076 A1 Jun. 23, 2011

(30) Foreign Application Priority Data

Dec. 21, 2009 (EP) ..................................... 09425520

(51) Int. Cl.
*H04N 7/00* (2011.01)
*H04N 5/20* (2006.01)
*G08G 1/00* (2006.01)

(52) U.S. Cl.
USPC ............. 348/148; 382/104; 340/932; 348/28; 348/143

(58) Field of Classification Search
USPC ............................. 348/148; 382/104; 340/932
See application file for complete search history.

(56) References Cited

U.S. PATENT DOCUMENTS

| | | | |
|---|---|---|---|
| 7,518,099 B2* | 4/2009 | Pallaro et al. | 250/221 |
| 2012/0142086 A1* | 6/2012 | Haguet et al. | 435/288.7 |

FOREIGN PATENT DOCUMENTS

| | | |
|---|---|---|
| DE | 30 23 444 | 1/1981 |
| DE | 40 08 280 | 9/1991 |
| DE | 195 06 550 | 8/1996 |
| DE | 197 47 017 | 4/1999 |
| EP | 1 418 089 | 5/2004 |
| EP | 1 635 163 | 3/2006 |
| EP | 1 764 835 | 3/2007 |
| EP | 1 976 296 | 10/2008 |

OTHER PUBLICATIONS

Search Report for EP 09425520.5 dated May 10, 2010.

* cited by examiner

*Primary Examiner* — Sath V Perungavoor
*Assistant Examiner* — Howard D Brown, Jr.
(74) *Attorney, Agent, or Firm* — Nixon & Vanderhye P.C.

(57) ABSTRACT

An optical detection system per motor-vehicles, suitable to detect the condition of the road surface on which the vehicle is travelling, comprising a photodetector unit composed of a camera having a matrix of pixels composed of photodetectors based on a photosensitive material suitable to detect both radiations in the visible and near infrared, i.e. having a wavelength comprised between 380 and 900 nanometres, and radiations in the short wavelength infrared, i.e. having a wavelength comprised between 900 and 1700 nanometres.

13 Claims, 4 Drawing Sheets

OPTICAL DETECTION SYSTEM FOR MOTOR-VEHICLES HAVING MULTIPLE FUNCTIONS, INCLUDING DETECTION OF THE CONDITION OF THE ROAD SURFACE

BACKGROUND OF THE INVENTION

The present invention refers to optical detection systems for motor-vehicles, of the type able for detecting the condition of the road surface on which the vehicle is travelling in such a manner to distinguish, for example, between a dry, wet, snow-covered or ice-covered surface.

In particular, the invention regards a system of this type comprising:
- a photodetector unit mounted on board the motor-vehicle, for receiving the electromagnetic radiation diffused by the road surface, and
- a control and processing electronic unit, suitable for receiving signals output from said photodetector unit and processing them with the aim of determining the condition of the road surface.

This type of detection system, which employs an emitter unit for lighting the road surface to be detected, was proposed in the European patent application EP 08 425 784.9 of the same Applicant, filed on Sep. 12, 2008 and still not open to public inspection as of date of filing of the present application.

SUMMARY OF THE INVENTION

The object of the present application is that of providing a system of the type specified above that is characterised by a high operational reliability and detection accuracy, the system in question being relatively simple and simultaneously suitable to also serve one or more further detection functions useful when driving the motor-vehicle.

In order to attain such object, the invention has the object of an optical detection system having the characteristics outlined above and further characterised in that said photodetector unit is a camera having a matrix of pixels composed of photodetectors based on a material, preferably InGaAs or Ge/Si, suitable to detect both radiations in the visible and near infrared (NIR), i.e. having a wavelength comprised between 380 and 900 nanometres, and radiations in the short wavelength infrared (SWIR), i.e. having a wavelength comprised between 900 and 1700 nanometres, in that said camera comprises a matrix of filters placed in front at least one part of the matrix of pixels in such a manner that each filter transmits the radiation to one and only one pixel of the matrix, and in that the matrix of filters comprises subgroups of four positions, wherein two positions are occupied by band-pass filters with respective wavelengths centred on values at which the radiation is absorbed respectively by water and by ice, and two positions are without filters, in such a manner to allow complete passage of the spectral band.

In the preferred embodiment, the above-mentioned control and processing electronic unit is programmed to control addressing of the pixels of the matrix ("windowing, window-of-interest readout" technique) of the camera to acquire at least three images: a first and a second image corresponding to the wavelengths wherein the radiation is respectively absorbed by water and ice, and at least a third image with full or partial spectral content in the band from the visible to the SWIR.

The control and processing electronic unit is programmed to perform linear and interpolation operations through known methods (for example nearest neighbour, linear, cubic, and cubic spline) among the abovementioned images for each pixel of the matrix of the camera with the aim of detecting the condition of the road surface.

In a specific embodiment, the control and processing unit is programmed to calculate, for each pixel of the camera matrix, the ratios between the intensity of said first and said second image with respect to the intensity of said third image and for detecting—regarding each of said ratios—the condition of the road surface according to a reference map.

The specific characteristics of the camera make the latter suitable to meet, alongside the function of detecting the condition of the road surface, other useful functions when driving a motor-vehicle. Therefore, in the preferred embodiment of the invention, the abovementioned control and processing electronic unit is programmed to use the above-mentioned third image to meet one or more further preventive safety functions selected from among:
- lane departure warning (LDW),
- high beam alignment (HBA),
- traffic signal recognition (TSR),
- night vision (NV),
- collision avoidance and mitigation (CAM), and
- pre-crash warning and intervention (PCWI).

BRIEF DESCRIPTION OF THE DRAWINGS

Further characteristics and advantages of the invention shall be clear from the following description with reference to the attached drawings, strictly provided for exemplifying and non-limiting purposes, wherein.

DETAILED DESCRIPTION OF THE INVENTION

Figure 1:
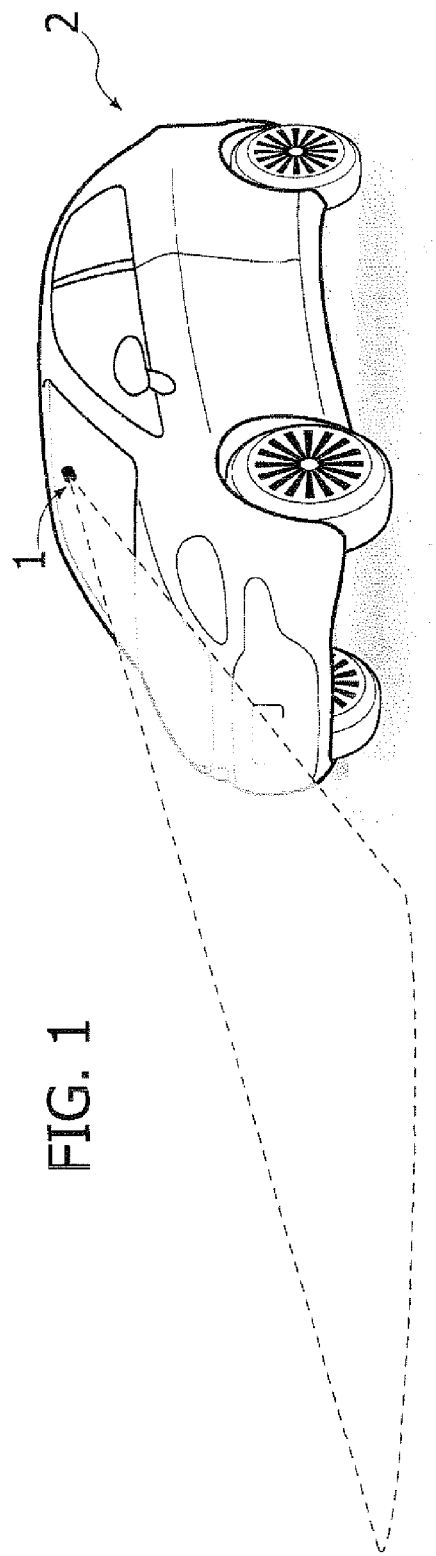
FIG. 1 is a schematic view of a motor-vehicle provided with a system according to the invention.

An essential component of the optical detection system according to the present invention is represented by a camera 1 with InGaAs or Ge/Si matrix of pixels, which is for example positioned in the cabin of a motor-vehicle 2 (see FIG. 1) at position immediately at the back of the windshield, and supported for example by the rear-view mirror structure inside the motor-vehicle.

Figure 2:
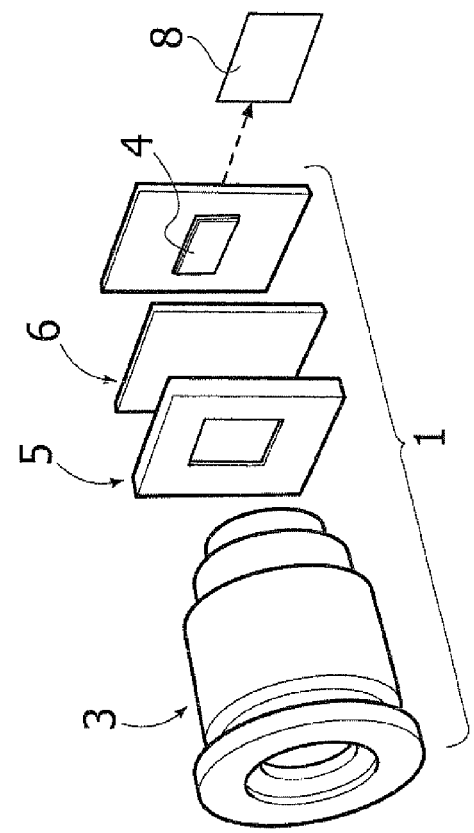
FIG. 2 is an exploded perspective view of the camera and of the control and processing electronic unit part of the system according to the invention.

An exemplifying configuration of the optical detection system is illustrated in FIG. 2 indicated in which is an exploded view of the camera 1, where the reference number 3 indicates a multispectral objective, suitable to minimize the chromatic aberrations and maximize transmittance in the spectral band from the visible to the SWIR, and reference number 4 indicates a matrix of pixels composed of photodetectors based on InGaAs or Ge/Si, suitable to detect both radiations in the visible and near infrared (NIR), i.e. having a wavelength comprised between 380 and 900 nanometres, and radiations in the short wavelength infrared (SWIR), i.e. having a wavelength comprised between 900 and 1700 nanometres. Reference number 5 indicates a package for the vision sensor including the glass lid characterised in that it is provided with antireflection coating suitable to maximize transmittance in the spectral band from the visible to the SWIR, while reference number 6 indicates a matrix of optical filters obtained on the surface of the matrix of pixels 4 according to the known art and which shall be described in detail hereinafter.

The camera 1 has an architecture known to those skilled in the art, which comprises a bias generator, time generator, column and line amplifiers, "shift registers", "gain", "offset" and analogue/digital converter. This architecture transforms signals output from the photodetectors into a high dynamic digitized image (e.g. 120 db) which is sent to a processing and control electronic unit indicated with reference number 8.

Figure 3:
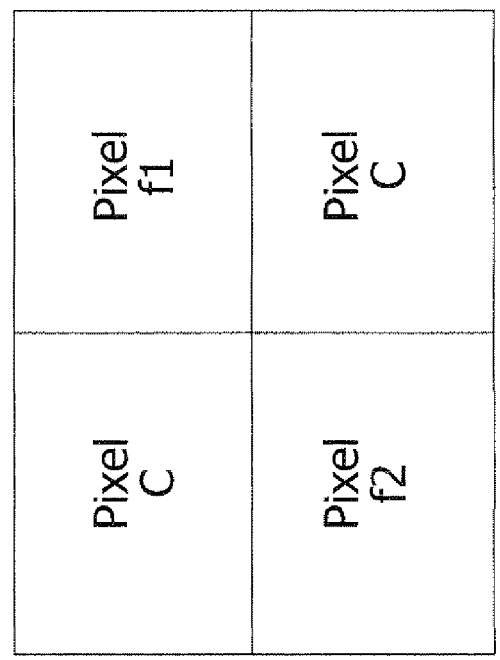
FIG. 3 is a typical spectral reference curve for band-pass filters.
Figure 4:
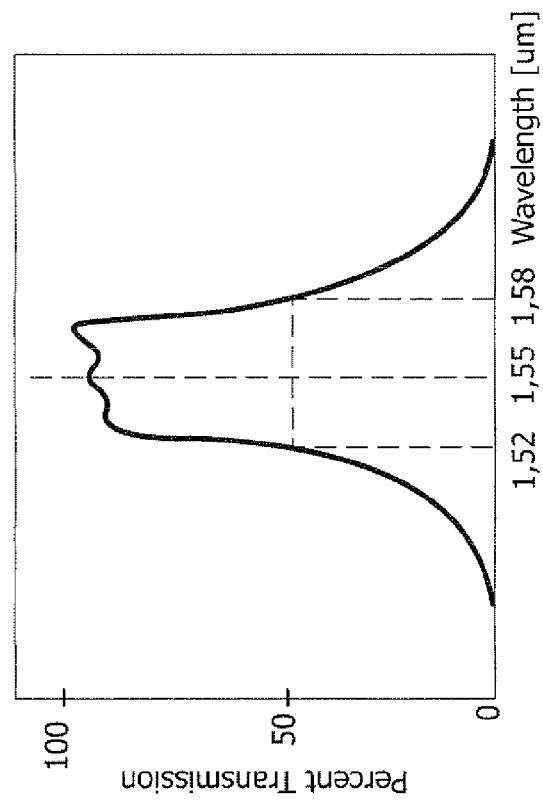
FIG. 4 is a schematic representation of the subgroup of the matrix of optical filters part of the camera of the system according to the invention, wherein two positions are occupied by band-pass filters $f_1$, $f_2$ and two positions c are without filters in such a manner to allow complete passage of the band.

The matrix of filters 6 comprises four-positions subgroups, wherein two positions are occupied by band-pass filters $f_1$, $f_2$ with the typical spectral response curve indicated in FIG. 3, with respective wavelengths centred on values at which the radiation is respectively absorbed by water and ice, and two positions c without filters in such a manner to allow complete passage of the band (see FIG. 4).

Contrary to other systems, such as for example the one proposed in the previous application of the same Applicant identified above, the system according to the present invention does not employ an electromagnetic radiation emitter unit suitable to direct such radiation towards the road surface, exclusively dedicated to determine the condition of the road surface.

As a matter of fact, given the high sensitivity of the photosensitive matrix in the spectral range of use, should the lighting be such to require the driver of the vehicle to use lighting means, with the aim of determining the condition of the road surface, halogen projectors—with which the motor-vehicle is equipped—are sufficient to light the portion of the road ahead of the vehicle.

Should the projectors be of the LED type, the optical detection system requires IRLED illuminators needed to serve other preventive safety functions such as, for example, the night vision (NV) function.

The aforedescribed configuration of the matrix of filters 6 (see FIG. 5) is such that each filter transmits radiation to one and only one pixel of the matrix.

The processing and control electronic unit 8 is programmed to control pixels of the matrix 4 of the camera to acquire at least three images: a first image and a second image corresponding to the wavelengths wherein the radiation is respectively absorbed by water and ice and at least a third image with full or partial spectral content in the band from the visible to the SWIR.

The control unit 8 is programmed to perform linear and interpolation operations, through known techniques (for example nearest neighbor, linear, cubic, and cubic spline), of the abovementioned images for each pixel of the camera matrix and hence detect the condition of the road surface.

Figure 8:
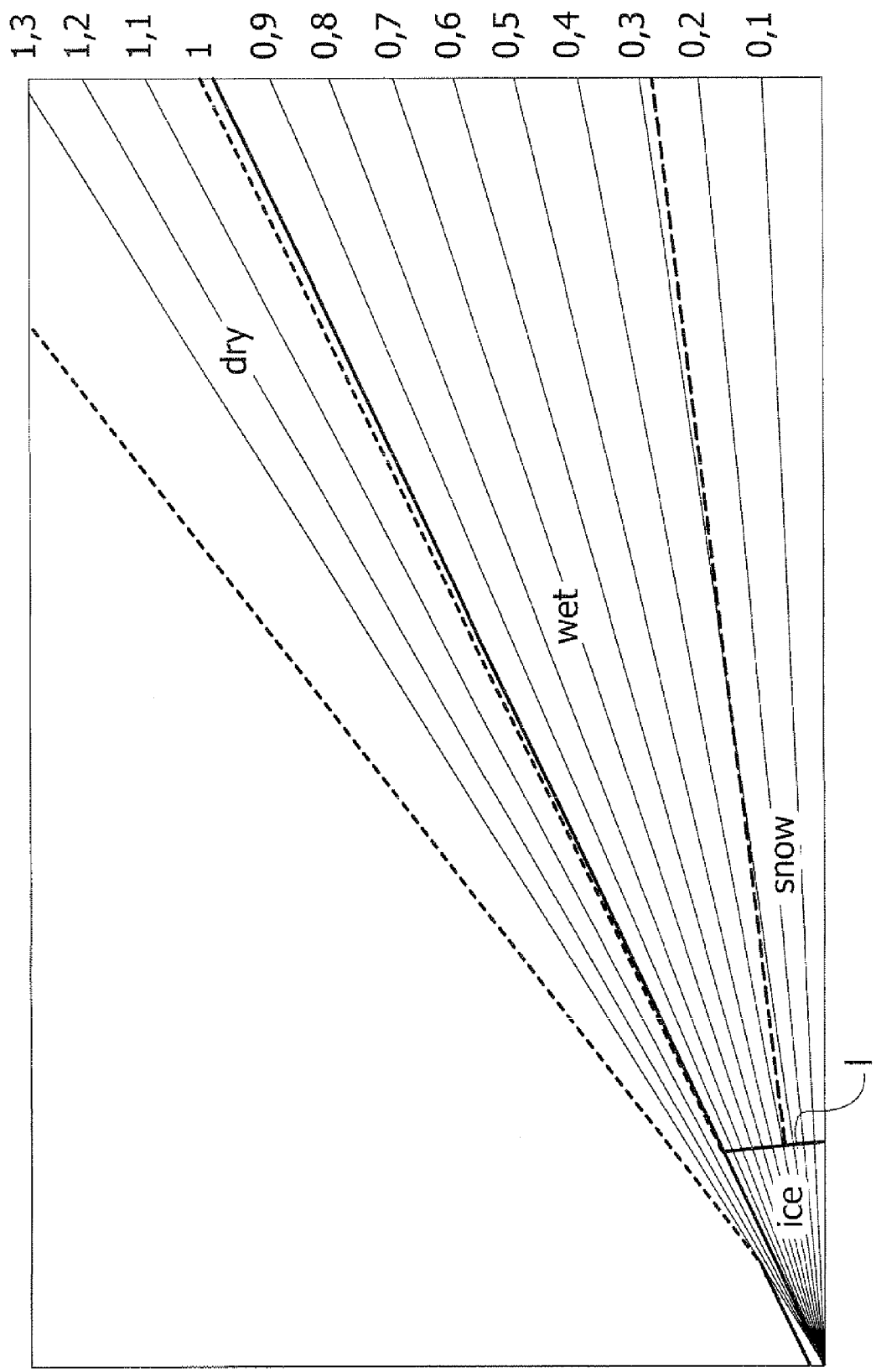
FIG. 8 illustrates a reference map in which the evaluation of the condition of the road surface is based in an embodiment of the system according to the invention.

In a preferred embodiment, the control unit calculates, for each pixel of the matrix 4 of the camera 1, the ratios between the intensity of said first image and said second image with respect to the intensity of said third image and to detect the condition of the road surface for each of such ratios, according to a reference map which is illustrated in FIG. 8. The use of a reference map of this type as the criterion for evaluating the condition of the road surface was already proposed in the previous patent application of the Applicant indicated above, and still not open to public inspection as of date of filing of the present application. Such map is a cartesian plane wherein the values of the intensity of the abovementioned third image (i.e. the one with full or partial spectral content in the band from the visible to the SWIR), are indicated on two abscissae, while the values of intensity of the first and second image are indicated on the axis of the ordinates. The corresponding light intensity values of the abovementioned three images may therefore be identified, hence allowing identifying the points of the reference map of FIG. 6. As illustrated, the map is divided into areas corresponding to the various conditions of the road surface (dry, wet, ice, snow). As observable, the various areas are divided by straight lines converging in the origin of the axis, each line corresponding to a ratio between the light intensities indicated in the abscissa and in the ordinate. The values of the ratios corresponding to various lines are indicated on the right side of the diagram (it should be observed that the scales along the two cartesian axes are different, hence the line corresponding to ratio 1 is not inclined to 45°). According to an important characteristic, already illustrated in the previous application of the Applicant, the system is capable of distinguishing between wet or snow condition and ice condition due to the fact that provided for is at least one separation line l (see FIG. 6) which is transverse with respect to the abovementioned lines converging in the origin of the axes and which separates the area corresponding to "ice"—which is closer to the origin of the axes—from the area corresponding to water and snow.

Figure 5:
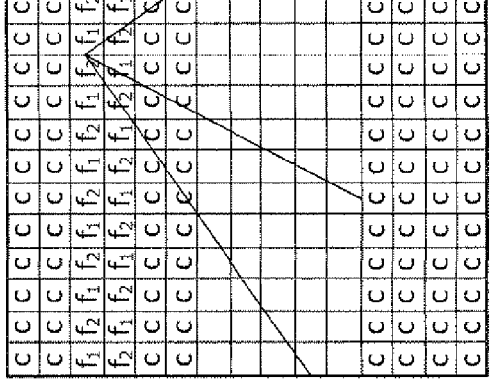
FIGS. 5-7 are alternative implementations of the matrix of optical filters part of the camera of the system according to the invention.

Furthermore, it should be observed that though the configuration of the matrix of filters illustrated in FIG. 5, where the filters extend over an area corresponding to the entire extension of the matrix of pixels 4, has the advantage of allowing obtaining multispectral images over the entire field of view of the vision system, it also has the disadvantage of a lower definition of the non-filtered image. Such drawback may be overcome by adopting the compromise represented by the configuration illustrated in FIG. 6, where the matrix of filters extends only over one or more portions of the matrix 4 of the camera that are in the field of view suitable to detect the condition of the road surface.

Figure 6:
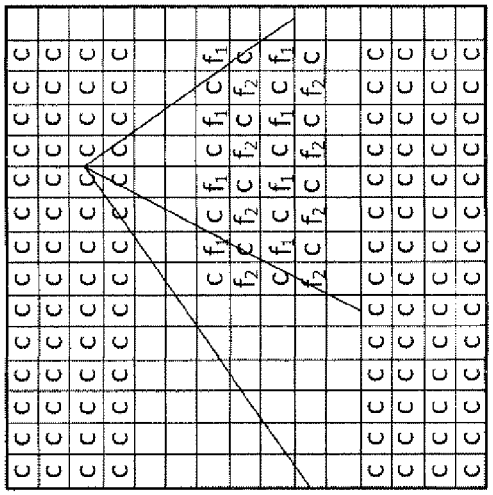
Figure 7:
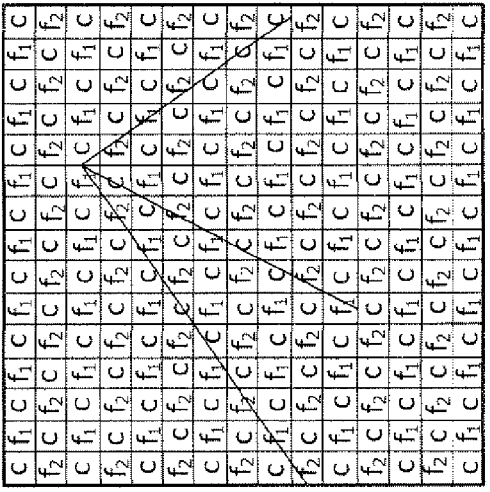

Another alternative solution is illustrated in FIG. 7, where the filters are prearranged only at one line, or only at some lines, of the matrix of photodetectors, that are dedicated to the detection of the condition of the road surface, full information regarding such condition being obtained in this case through the movement of the vehicle. It should be observed that also schematically represented in FIGS. 5-7 is the road ahead of the vehicle.

The specific characteristics of the optical detection system are such to allow application thereof also to meet other detection functions regarding preventive safety, in addition to those of detecting the condition of the road surface. The abovementioned third image—acquired by the camera with full or partial spectral content in the band from the visible to the SWIR—is used for such additional functions. The acquired image is processed to meet one or more further detection functions selected from among:

lane departure warning or LDW,
    high beam alignment (HBA),
    traffic signal recognition (TSR),
    night vision (NV),
    collision avoidance and mitigation (CAM),
    pre-crash warning and intervention (PCWI).

In a practical embodiment, the method for detecting the condition of the road surface consists of:

1. acquiring an image,
2. intervening on the addressing of the pixels in such a manner to make useable at least the abovementioned first, second and third image,
3. adapting the intensity to guarantee maximum contrast for one or more images,
4. using the image with full or partial spectral content in the band from the visible to the SWIR and applying algorithms for the identification of the road lane and resize the image in such a manner that the region of interest is within the lane,
5. executing the ratio—pixel by pixel—between the images corresponding to the wavelengths wherein there is absorption by water and ice and that having complete spectral content,
6. applying a low-pass digital filter to eliminate discontinuity on the image obtained in step 5,
7. extracting contours in such a manner to highlight the areas with water or ice,
8. indicating the intensity value of the image obtained on the reference map of FIG. 6 and establish the condition of the road corresponding to each zone highlighted in step 7.

According to another preferred characteristic, the optical detection system is prearranged to provide data regarding the state of the condition of the road in correlation with the value of the environmental temperature sensor present on the vehicle ad use of the air conditioning function. The data may be compared—according to known decision strategies—by the processing and control electronic unit 8, in a control unit on board the vehicle or in a dedicated electronic unit.

According to a further preferred characteristic, the optical detection system is prearranged to be optimised and used with the CAM and PCWI preventive safety functions. As a matter of fact, information provided regarding the condition of the road provided for by the abovementioned system allows optimising the algorithms used by the system for controlling and preparing braking depending on the grip conditions of the vehicle.

According to a further preferred characteristic, the optical detection system is conceived to be used for the validation of or in correlation with grip evaluation obtained by the sensors provided for controlling and monitoring the lateral and longitudinal dynamic of the vehicle.

Obviously, without prejudice to the principle of the invention, the details and embodiments may vary, even significantly, with respect to what has been described herein by way of non-limiting example only, without departing from the scope of the present invention.

What is claimed is:

1. Optical detection system for motor-vehicles, able to detect the condition of a road surface on which a vehicle is travelling, said system comprising:
   a photodetector unit mounted on board the motor-vehicle, for receiving a electromagnetic radiation diffused by the road surface, and
   a control and processing electronic unit, suitable to receive signals output from said photodetector unit and to process them with the aim of detecting the condition of the road surface, said system being characterised in that said photodetector unit is a chamber having a matrix of pixels composed of photodetectors based on a material, preferably InGaAs or Ge/Si, suitable to detect both radiations that are visible and near infrared, wherein the radiation has a wavelength comprised between 380 and 900 nanometres, and radiations in the short wavelength infrared (SWIR), has a wavelength comprised between 900 and 1700 nanometres,
   wherein the optical detection system comprises a matrix of filters arranged before at least one part of the matrix of pixels in such a manner that each filter transmits the radiation to one and only one pixel of the matrix, and
   in that the matrix of filters comprises four-positions subgroups, wherein two positions are occupied by bandpass filters with respective wavelengths centred on values at which the radiation is respectively absorbed by water and ice, and two positions are without filters, to allow complete passage of a spectral band.

2. System according to claim 1, wherein said control and processing electronic unit is programmed to control and addressing of the pixels of the matrix for the acquisition of at least three images: a
   first image and a second image corresponding to the wavelengths wherein the radiation is respectively absorbed by water and ice, and at least a third image with full or partial spectral content in the band from the visible to the SWIR.

3. System according to claim 2, wherein said control and processing electronic unit is programmed to process a first image, a second image and a third image for each pixel of the matrix and hence detect the condition of the road surface.

4. System according to claim 3, wherein said control and processing electronic unit is programmed to calculate, each pixel of the matrix, a ratios between a intensity of said first image and said second image with respect to a intensity of said third image and to detect the condition of the road surface according to a reference map.

5. System according to claim 4, wherein said reference map is a cartesian plane wherein the intensity values of said third image are indicated on a first cartesian axis, the intensity values of said first image and said second image are indicated on a second cartesian axis, and wherein such cartesian plane is divided into subareas identified a priori as corresponding to different conditions of the road surface.

6. System according to claim 5, wherein in said reference map the border lines that divide such subareas from each other comprise both line portions converging radially towards the origin of the cartesian axes, and line portions directed transversely with respect to said radial line portions, one of said transverse line portions separating a region of the map corresponding to the presence of ice on the road surface from regions corresponding to presence of water or snow on the road surface.

7. System according to claim 2, wherein said control and processing electronic unit is programmed to use said third image in such a manner to meet one or more further preventive safety functions selected from among:
   lane departure warning or LDW,
   high beam alignment,
   traffic signal recognition,
   night vision,
   collision avoidance and mitigation, and
   pre-crash warning and intervention.

8. System according to claim 1, wherein said matrix of filters is placed in front of an entire extension of said matrix of photodetectors.

9. System according to claim 1, wherein said matrix of filters is placed only in front of a portion of said matrix of photodetectors which is dedicated to the detection of the condition of the road surface.

10. System according to claim 1, wherein said matrix of filters is placed only in front of one line, or some lines, of said matrix of photodetectors which are dedicated to the detection of the condition of the road surface, complete information regarding the condition of the road surface being obtained when the vehicle is moving.

11. System according to claim 7, wherein said control and processing electronic unit is programmed to provide information regarding the condition of the road surface to the algorithms of the CAM and PCWI functions.

12. System according to claim 7, wherein said control and processing electronic unit is programmed to provide information regarding the condition of the road for estimating the grip of the vehicle against the road in systems for controlling a lateral and longitudinal dynamic of the vehicle.

13. System according to claim 1, wherein said control and processing electronic unit is programmed to provide information regarding the condition of the road in correlation with a value of an environmental temperature sensor.

\* \* \* \* \*